United States Patent [19]

Inbar et al.

[11] 4,095,108
[45] June 13, 1978

[54] SIGNAL PROCESSING EQUIPMENT FOR RADIATION IMAGING APPARATUS

[75] Inventors: Dan Inbar, Haifa; Yitzhak Klein, Kirvat Yam, Haifa, both of Israel

[73] Assignee: Elscint Ltd., Haifa, Israel

[21] Appl. No.: 723,620

[22] Filed: Sep. 14, 1976

[30] Foreign Application Priority Data

Sep. 17, 1975 Israel .................................. 48111

[51] Int. Cl.² .......................... G01T 1/20; G01T 1/164
[52] U.S. Cl. ................................. 250/369; 250/363 S
[58] Field of Search .............................. 250/363 S, 369

[56] References Cited

U.S. PATENT DOCUMENTS

| 3,714,429 | 1/1973 | McAfee et al. | 250/363 S |
|---|---|---|---|
| 3,862,425 | 1/1975 | Myers | 250/363 S |
| 3,953,735 | 4/1976 | Stout | 250/363 S |

Primary Examiner—Archie R. Borchelt
Attorney, Agent, or Firm—Donald M. Sandler

[57] ABSTRACT

Coordinates of a light event, computed by signal processing equipment from output signals developed by an array of photodetectors of radiation imaging apparatus in response to the interaction of a radiation stimulus with a scintillation crystal, are validated only if a representation of the total energy of the light event lies within an energy window functionally related to the coordinates of the light event. In this manner, only desirable radiation stimuli interacting with the crystal are detected, and undesirable, indirect or scattered radiation stimuli interacting with the crystal are discriminated against.

5 Claims, 6 Drawing Figures

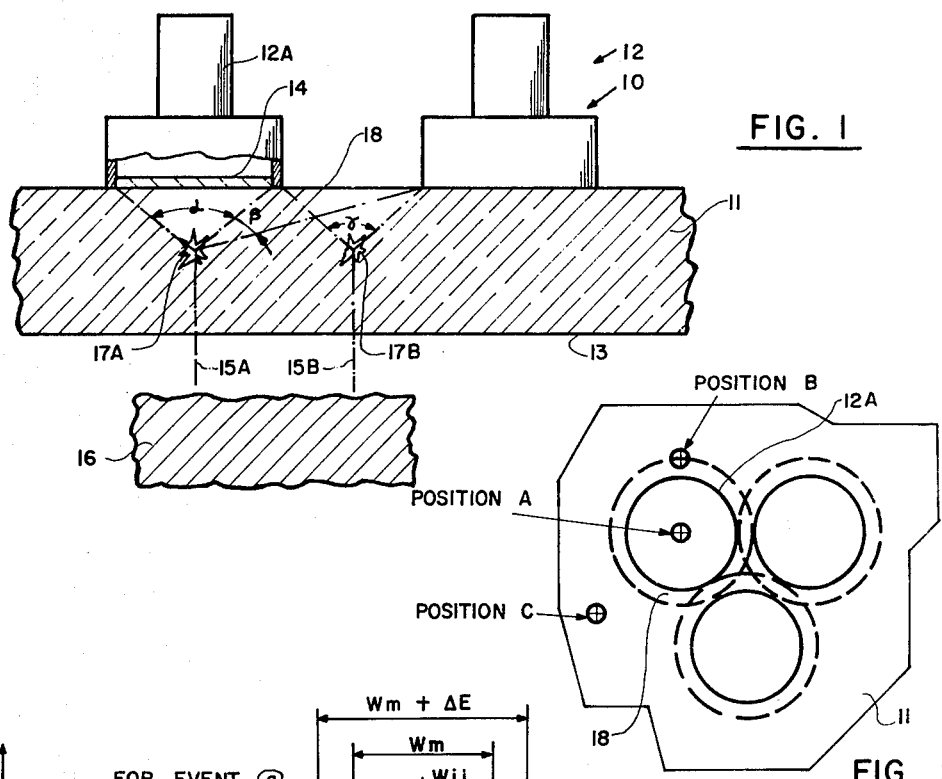
FIG. 1
FIG. 2
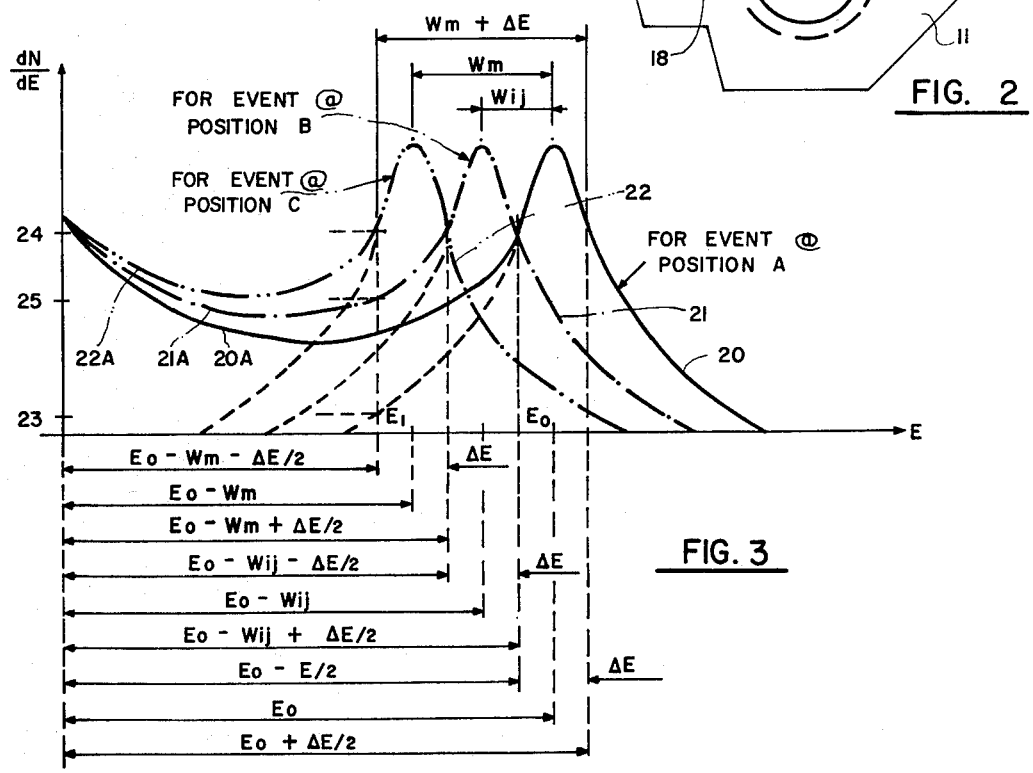
FIG. 3

SIGNAL PROCESSING EQUIPMENT FOR RADIATION IMAGING APPARATUS

BACKGROUND OF THE INVENTION

This invention relates to signal processing equipment for radiation imaging apparatus such as an Anger-type gamma camera disclosed in U.S. Pat. No. 3,011,057.

A conventional Anger-type gamma camera comprises a scintillation crystal responsive to radiation stimuli for producing light events at spatial locations corresponding to the locations at which the stimuli interact with the crystal, and a plurality of photodetectors arranged in a predetermined array with respect to the crystal for viewing light events therein and producing output signals in reponse thereto.

Associated with a gamma camera is signal processing equipment including means responsive to the output signals for generating an energy signal representative of the total energy of the light event producing such signals, and coordinate computation circuitry, responsive to the output signals of the photodetectors of the camera produced in response to the occurrence of a light event in the crystal, for computing the spatial coordinates of the light event provided the energy signal lies within a predetermined energy window.

Gamma cameras of the type described above are well known in the art and are in wide use in the nuclear medicine field for the purpose of obtaining pictures of the distribution of radioactivity in an object under investigation such as an organ of the human body containing a diagnostic quantity of a radioactive tracer. Depending upon the type of tracer utilized, all direct radiation stimuli originating in the organ will have a predetermined energy level, as for example 120 Kev. In addition to direct radiation incident on the scintillation crystal at a known energy level due to the tracer present in the organ under study, other types of radiation stimuli are also incident on the crystal and interact therewith. For example, background radiation, as from cosmic radiation, will always be present and will interact with the crystal. In addition, radiation stimuli resulting from the scattering of direct radiation stimuli originating from the tracer will also be incident on the scintillation crystal. These scattered radiation stimuli include the so called Compton products resulting from the interaction of direct radiation stimuli with soft tissue in the human body.

Since the direct radiation stimuli arriving in the crystal have a predetermined energy level, the scattered radiation stimuli can be discriminated against by passing the energy signal produced by the signal processing equipment associated with a camera through a single channel analyzer having an energy window comprehending the energy level associated with the tracer being utilized. Because of statistical variations in the number of photons created in each light event due to the interaction of a radiation stimulus with the scintillation crystal, the size of the energy window may be as large as 20% of the known energy level associated with the tracer in order to provide for the detection of a usable number of events. However, it is usually the case that the size of the window is so large that scattered radiation stimuli interacting with the crystal are detected and considered as if such events were produced by direct radiation stimuli. This situation is partially responsible for the spatial non-homogeneity of gamma cameras; and it is an object of the present invention to provide new and improved signal processing equipment for use with such cameras wherein compensation is provided for spatial non-homogenity.

SUMMARY OF THE INVENTION

The present invention provides signal processing equipment for use with radiation imaging apparatus of the type having a scintillation crystal responsive to radiation stimuli for producing light events at spatial locations corresponding to the locations at which the stimuli interact with the crystal, and a plurality of photodetectors arranged in a predetermined array with respect to the crystal for viewing light events therein and producing output signals in response thereto. The signal processing equipment includes means responsive to the output signals for generating an energy signal representative of the total energy of the light event producing such signals. In addition, the signal processing equipment includes coordinate computing circuitry responsive to the output signals produced by the occurrence of a light event for computing its spatial coordinates. The improvement in the signal processing equipment relates to means for validating the computed coordinate of a light event only if the energy signal lies within an energy window functionally related to the coordinates of the light event.

It has been determined that the amount of light received by the photo sensitive surfaces of the photodetectors in the array for a given interaction of a radiation stimulus of fixed energy with the crystal, varies as a function of the position of the light event in the plane of the crystal. For example, the number of photons received when a light event occurs directly within the projected area of the photo sensitive surface of a photodetector on the crystal will usually be different from the number of photons received when the light event occurs in an annular region surrounding the projection of the photo sensitive surface on the crystal. For light events of the latter type, more of the photons either escape from the crystal or are absorbed therein without contributing to the output signals of the photodetectors.

The variation in the number of photons detected by a photodetector as a function of the position of the light event with respect to the photodetector causes the energy signal, which is representative of the total energy of the light event, to be functionally dependent on the position of the light event in the plane of the crystal. As a consequence, this functional dependence on the energy signals on the position of the light events in the plane of the crystal causes the single channel analyzer to incorrectly accept or reject light event thereby reducing the fidelity of images derived from the output of the coordinate computation circuitry.

The above described problem is avoided by the present invention because the validation of the computation of the coordinates of a light event is made dependent upon the relationship between the energy signal associated with a light event and a predetermined energy window dependent on the coordinates of the light event.

BRIEF DESCRIPTION OF THE DRAWINGS

Embodiments of the present invention are illustrated in the accompanying drawings wherein:

FIG. 1 is a cross section of a portion of a conventional gamma camera for the purpose of illustrating the sensitivity of the position of a light event in the plane of the crystal on the amount of light received by a photodetector;

FIG. 2 is a plan view of a portion of an array of photo multipliers of a conventional gamma camera;

FIG. 3 shows the probability density function for events occurring at different locations in a crystal with respect to the photodetector array;

DETAILED DESCRIPTION

Figure 4:
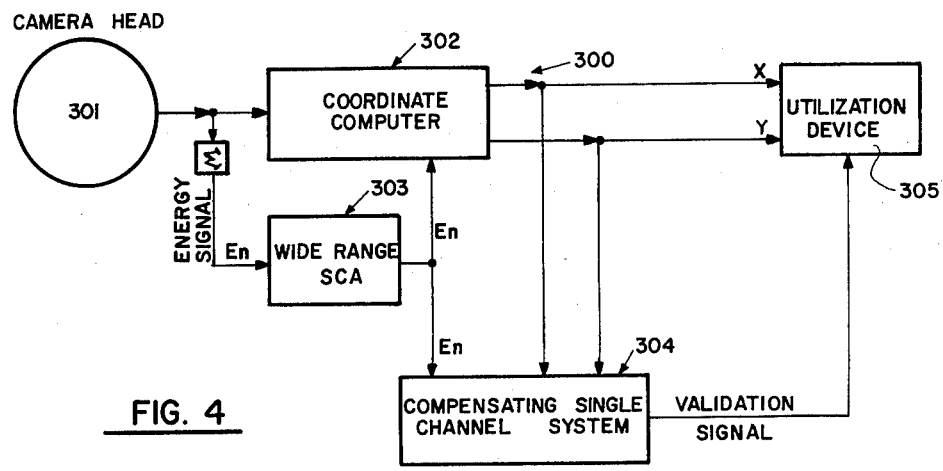
FIG. 4 is a block diagram of signal processing equipment according to the present invention for validating the computed coordinates.

Referring to FIG. 1, reference numeral 10 designates conventional radiation imaging apparatus in the form of an Anger-type gamma camera whose significant components so far as the present invention is concerned includes scintillation crystal 11 and a plurality of photomultiplier tubes 12. In actual practice, a collimator (not shown) is positioned adjacent surface 13 for passing to this surface radiation stimuli directed normal to the plane of this surface, and light coupling means (not shown) are interposed between the crystal and the photo cathodes 14 of the photomultiplier tubes. As is well known, such light coupling means includes a glass cover for the crystal and an overlying plastic light pipe for conveying light from the crystal to the photomultiplier tubes. These last mentioned components are not shown in order to simplify the drawing.

Radiation stimuli 15A and 15B from a source, such as a human organ containing a diagnostic quantity of a radioactive tracer, for example, shown schematically at 16, directed normal to the plane of surface 13, enter crystal 11; and there is a high probability the stimuli will interact with the crystal producing light events 17A and 17B bearing the same spatial relationship to each other as the points in organ 16 from which the stimuli originated. Usually there is a finite time difference between the occurrence of events 17A and 17B, but both are shown together in the drawing for convenience.

While only two photomultipliers are shown in FIG. 1, it is conventional to employ nineteen arranged in a 3-4-5-4-3 hexagonal pattern such that photocathodes of the tubes face the crystal and view light events occurring therein. The photomultipliers have overlapping fields of view and a light event anywhere in the crystal is seen by all of the tubes which respond by producing output signals. Each output signal is integrated to provide a measure of the energy received by a tube due to a light event; and processing of the output signals, for example, as shown in U.S. Pat. No. 3,011,057 or copending Application Ser. No. 503,767 filed Sept. 6, 1974 yields the coordinates of the light event.

Direct radiation stimuli from the organ (i.e., direct stimuli resulting from the radioactive tracer) arrives at an energy level determined by the tracer of tracer involved. For example, the tracer may be such as to provide stimulti at 120 Kev. In addition to receiving direct radiation stimuli from the tracer, the crystal also receives background radiation stimuli from cosmic rays, and so called Compton products resulting from scattering caused by the interaction of stimuli from the tracer with soft tissue and other material surrounding organ 16; and these stimuli also interacts with the crystal producing light events. As is well known, light events from background stimuli and from Compton products can be distinguished from light events due to direct stimuli from the tracer in terms of the energy of the light event, this discrimination being carried out by a single channel analyzer (SCA) in the signal processing equipment associated with the camera. Ideally, the SCA would validate only those events whose energy is associated with the tracer being used.

For the reasons indicated below, the SCA must provide an energy window for validating light events whose energy lies within the window which can be as large as 20–25% of the energy associated with the tracer being used. A window is required because of statistical variations in the number of photons emitted from light events caused by stimuli of the same energy.

It has been discovered that the total light (i.e., energy) received by the photomultipliers from a light event caused by a stimulus of predetermined energy is dependent on the coordinate location of the light event in the crystal. Consequently, the energy window of the SCA must be wide enough to accomodate variations in energy arising out of the event locational dependency of the amount of light received by the array of photomultipliers. By reason of the window size, light events caused by scattered radiation stimuli with energy lying within the window are treated by the signal processing equipment as direct radiation stimuli originating from the organ under investigation. No amount of light coupling means modifications or corrections to individual output signals based on the location of the event can correct or compensate for light events from scattered radiation being considered as events from direct radiation. The problem is complicated, moreover, by the variable nature of scattering phenomena from patient to patient and from one organ to another organ.

The coordinate location dependency of the energy signal received by the photomultipliers is illustrated in FIG. 1. Light event 17A occurs centrally with respect to photocathode 14 of tube 12A within the volumetric projection of the photocathode on the crystal; and all of the light within the cone of solid angle $\alpha$ is incident on the photocathode. Light within the annular cone of solid angle $\beta$ is incident on the annular region 18 between adjacent tubes, and such light is reflected back into the crystal or absorbed. Reflected light is received by other tubes remote from the event reducing the effectiveness of their outputs to computational accuracy and also causes non-uniformity of the total light received by the P.M. array.

Light event 17B occurs midway between adjacent photomultipliers, and all of the light within the cone of solid angle $\gamma$ is incident on the region of the crystal between adjacent tubes, and is lost so far as accurate computational results are concerned. Obviously, optical limitations are present in any array of photomultipliers and discontinuities; and non-uniformities exist in their light sensitive surfaces, all of which contribute to the locational sensitivity of the total number of photons received by the array from a light event of given energy.

If a large number (N) of radiation stimuli of fixed energy ($E_o$) were incident on the crystal at position A (FIG. 2), which is aligned with the optical axis of tube 12A, and the output signal from all of the tubes were integrated to provide a measure of the energy of each light event produced by the stimuli, it would be found that the cumulative distribution of events would be a function of energy. The peak of distribution would be close to the fixed energy $E_o$; and the probability density function dN/dE would have the form shown by peaked-curve 20 of FIG. 3 which is symmetrical about $E_o$. Roughly speaking, the ordinate dN/dE of the curve at any energy E gives the probability of obtaining an event at that energy.

By carrying out the above operation at other points spaced from position A (FIG. 2), and particularly at positions B and C, for example, in the annular region of the crystal surrounding tube 12A, other probability density distributions will be obtained. In general, each will peak at values of energy lower than $E_o$; and curves 21 and 22 represent two other typical distributions. Curve 22 is the curve displaced the maximum from curve 20 (the displacement being given by the energy $W_m$) and is based on stimuli incident at a particular distance and azimuth from position A.

Curve 21 is representative of a probability density function intermediate curves 20 and 21, typically one which would result for radiation incident on the crystal at a point $x, y$ (e.g., position B). Its peak is displaced from the peak of curve 20 by the energy $W_{ij}$.

The symmetrical curves 20, 21, 22 can be obtained by a calibration process using apparatus similar to that disclosed in U.S. Pat. No. 3,745,345. In this patent, an apertured mask is placed beneath the crystal for localizing the incidence on the crystal of radiation stimuli. Since the coordinates of each aperture are known, the computed coordinates of events can be compared with the actual coordinates, and a correction map can be made to provide compensation for the non-linear spatial response of the camera. Using a similar approach, probability density functions at various locations across the entire crystal can be obtained using a multichannel analyzer (i.e., an analyzer that will segregate the light events by their energy level). From these data, the value $W_{ij}$ at each of an array of points on the crystal can be found, as can be maximum value which is $W_m$.

Heretofore, the energy window of a SCA associated with signal processing equipment for a gamma camera would have been of width $W_m + \Delta E$ (which may be from 20 to 25% of $E_o$) in order to accomodate light events occurring at all possible coordinate locations in the crystal. The consequences of having such a large energy window can be seen by considering the effect on the probability density functions of the Compton products arising during actual use as distinguished from calibration use of a gamma camera. Referring again to FIG. 3, the tails 20A, 21A and 22A on respective curves 20, 21 and 22 represent the effects of scattered radiation stimuli. Thus, if the energy signal were: $E_l = E_o - W_m + \Delta E$ (i.e., at the lower limit of the window), the light event causing the tube array to receive energy would be considered as a valid event, and it would contribute to the display produced by the camera. Regardless of where the event took place, it would be considered valid by the signal processing equipment.

From FIG. 3 it can be seen that there is a relatively low probability that an energy signal $E_l$ would have resulted from an event at position A (FIG. 2). This probability is indicated at point 23 in FIG. 3. The highest probability indicated at point 24 is that the event occurred at position C. Assume, however, that the coordinate computation circuitry of the signal processing equipment associated with the camera has determined that the event with energy $E_l$ occurred at position A. In such case, the probability is greater for the event to have been the result of a scattered radiation stimulus (see point 25 in FIG. 3) than from a direct radiation stimulus (see point 23 in FIG. 3). In other words, the probability is that the event should not have been included in the display. Errors of the nature described above can be eliminated or substantially reduced by validating a light event (i.e., accepting an event as one resulting from direct radiation as distinguished from scattered radiation) only if the energy of the event as measured by the photomultipliers lies within an energy window functionally related to the coordinates of the event. For example, if the coordinate computation circuitry indicates that an event has occurred at position A (FIG. 2), the measured energy of the event (hereinafter termed $E_n$) must satisfy the relationship: $E_o - (\Delta E)/2 \leq E_n \leq E_o + (\Delta E)/2$. If $E_n$ had the value $E_l$ as shown in FIG. 3, (i.e., an energy for which the likelihood is that an event occurring at position A would be from a scattered radiation stimulus), the event would be discarded as probably not having been caused by a direct radiation stimulus.

On the other hand, if $E_n$ of a light event had the value $E_l$ and the computed coordinates placed the event at position C (FIG. 2), validation would be made because $E_n$ would satisfy the relationship: $E_o - W_m - (\Delta E/2) \leq E_n \leq E_o - W_m + (\Delta E)/2$. Thus, validation of a coordinate computation can be carried out event-by-event using the probability density functions obtained by the calibration process described above.

FIG. 4 shows signal processing equipment 300 according to the present invention for use with radiation imaging apparatus in the form of a conventional Anger-type gamma camera 301. Equipment 300 includes coordinate computing circuitry 302 for computing the coordinates of light events from the output signals furnished by camera head 301. Such circuitry can take any of the forms well known in the art. Also included in equipment 300 is a wide-range single channel analyzer 303 which receives the sum of all of the output signals from the photomultipliers of camera 301, i.e., $E_n$. The window in SCA 303 is set in accordance with the calibration results, namely from $E_o - W_m - (\Delta E)/2$ to $E_o + (\Delta E)/2$ defining a window opening of $W_m + \Delta E$. If $E_n$ passes through the window in SCA 303, circuitry 302 uses the energy of a light event to compute the normalized coordinates $x, y$ of the event. Both $E_n$ of the event and the coordinates thereof are applied to compensating single channel system 304 which determines whether $E_n$ satisfies the relationship:

$$E_o - W_{ij} - (\Delta E)/2 \leq E_n \leq E_o - W_{ij} + (\Delta E)/2 \quad (1)$$

where, it will be recalled, $W_{ij}$ is a parameter associated with an event at $x, y$ and obtained during the calibration. It should be understood that $W_{ij}$ will be an interpolated value for values $x, y$ not corresponding to the data points obtained during calibration.

Figure 5:
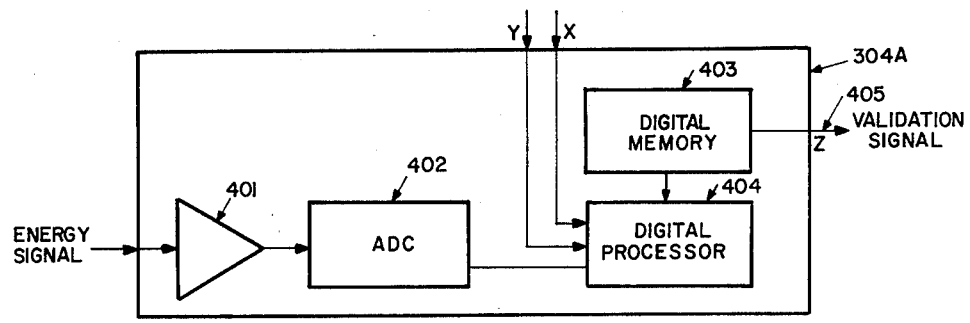
FIG. 5 is one embodiment of means for validating the computed coordinates.

Details of one embodiment of a compensating single channel system according to the present invention is designated by reference manual 304A in FIG. 5. System 304A includes a digital memory 403 containing $W_{ij}$ for each calibration point on the crystal. Digital processor 404 receives the computed coordinates $x, y$ from circuitry 302 and draws from memory 403 sufficient data to specify $W_{ij}$ for the computed coordinates.

Processor 404 also receives from analog-to-digital converter 402, a digital representation of energy signal $E_n$ which is first amplified at 40 therefore being applied to ADC 402. With $E_n$ of the light event and $W_{ij}$ of the coordinates $x, y$, processor 404 determines whether inequality (1) is satisfied. If it is, processor 404 issues a validation signal in line 405 which is used to enable utilization device 305 associated with equipment 300. such utilization device can be a CRT and line 405 can be used to unblank the election beam. Alternatively, device 305 can be a memory storage unit and a validating signal in line 405 can be used to enable a transfer of the coordinates from circuitry 302 into memory.

Figure 6:
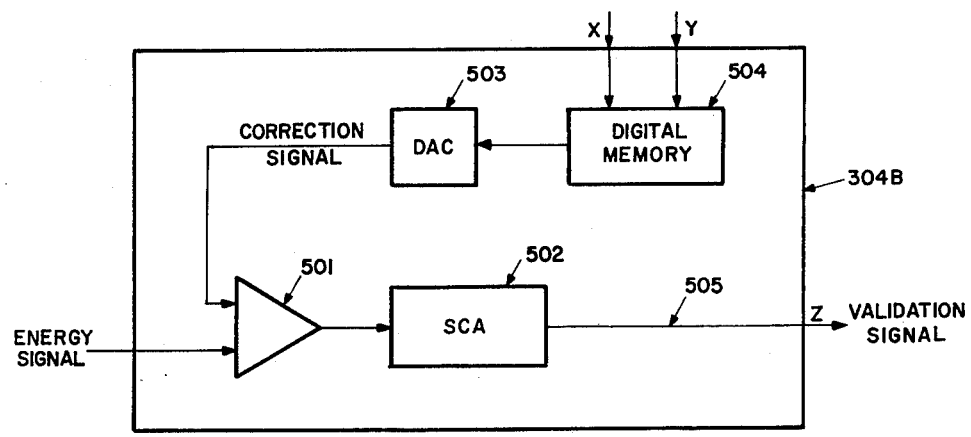
FIG. 6 is a second embodiment of the invention.

FIG. 6 shows a second embodiment 304B of system 304. In this embodiment, momory 504 contains correction factors as a function of $x$, $y$. Each correction factor, when applied to $E_n$ will convert it to a corrected energy signal $E_n'$. Application of the correction can be by way of either a factor that is added to or multiplied with $E_n$. For example, if an addition correction process is involved, the correction factor for an event at $x$, $y$ is $W_{ij}$, and this factor is applied to digital-to-analog converter 503 and added to $E_n$ in adder 501. The output of adder 501 is applied to SCA 502 when energy window is preset to pass signals in the range $E_o - (\Delta E)/2$ to $E_o + (\Delta E)/2$. Only if $E_n$ is proper for the coordinates of the event as determined from FIG. 3 will SCA 502 issue a validation signal on line 505.

While embodiments 304A and 304B disclose hybrid digital and analog system, it is believed apparent that the embodiments could be all digital or all analog.

It is believed that the advantages and improved results furnished by the apparatus of the present invention are apparent from the foregoing description of the several embodiments of the invention. Various changes and modifications may be made without departing from the spirit and scope of the invention as sought to be defined in the claims that follow.

What is claimed is:

1. In signal processing equipment for use with radiation imaging apparatus of the type having a scintillation crystal responsive to radiation stimuli for producing light events at spatial locations corresponding to the locations at which the stimuli interact with the crystal, and a plurality of photodetectors arranged in a predetermined array with respect to the crystal for viewing light events therein and producing output signals in response thereto, wherein the signal processing equipment includes means responsive to the output signals for generating an energy signal $E_n$ representative of the total energy of the light event producing such signals; and coordinate computation circuitry responsive to the output signals produced by the occurrence of a light event for computing its spatial coordinates, the improvement in the signal processing equipment comprising;
   means for validating the event only if $E_n$ lies within an energy window functionally related to the coordinates of the light event.

2. The invention according to claim 1 wherein the means for validating includes:
   (a) a single channel analyzer responsive to $E_n$ for enabling the coordinate computation circuitry of the signal processing equipment to compute the coordinates of the light event from output signals of the photodetectors only when $E_n$ lies within a relatively wide, predetermined energy window; and
   (b) a compensating single channel system responsive to $E_n$ and to the coordinate computed by the coordinate computation circuitry for producing a validity signal only if $E_n$ lies within an energy window functonally related to the coordinate of the light event.

3. The invention of claim 2 wherein the compensating single channel system includes storage means for storing a representation of the functional dependent of the energy window on event location.

4. The invention of claim 3 wherein the compensating single channel system includes means responsive to computation of the coordinates of a light event for withdrawing from the storage means, a representation of the particular energy window functionally related to such coordinates, and means responsive to the particular energy window for producing a validating signal only if $E_n$ falls within the particular energy window.

5. The invention of claim 2 wherein the compensating single channel system includes storage means for storing a representation of coordinate dependent compensation, means responsive to computation of the coordinates of a light event for withdrawing from the storage means, the representation of compensation dependency on the coordinates of the light event, means for applying the withdrawn representation of compensation to $E_n$ for generating $E_n'$, the corrected energy signal, and a single channel analyzer having a preselected energy window responsive to $E_n'$ for producing a validating signal only if $E_n'$ lies within the preselected energy window of the single channel analyzer.

* * * * *

REEXAMINATION CERTIFICATE (2460th)

United States Patent [19]

Inbar et al.

[11] B1 4,095,108

[45] Certificate Issued Jan. 31, 1995

[54] SIGNAL PROCESSING EQUIPMENT FOR RADIATION IMAGING APPARATUS

[75] Inventors: Dan Inbar, Haifa; Yitzhak Klein, Kirvat Yam, both of Israel

[73] Assignee: Elscint, Ltd., Haifa, Israel

Reexamination Request:
No. 90/003,451, Jun. 6, 1994

Reexamination Certificate for:
Patent No.: 4,095,108
Issued: Jun. 13, 1978
Appl. No.: 723,620
Filed: Sep. 14, 1976

[30] Foreign Application Priority Data

Sep. 17, 1975 [IL] Israel .................................. 48111

[51] Int. Cl.$^6$ ...................... G01T 1/208; G01T 1/164
[52] U.S. Cl. ............................ 250/369; 250/363.07
[58] Field of Search ........................... 250/363.07, 369

[56] References Cited

U.S. PATENT DOCUMENTS

| | | |
|---|---|---|
| 3,714,429 | 1/1973 | Mozley et al. |
| 3,862,425 | 1/1975 | Myers |
| 3,953,735 | 4/1976 | Stout |
| 4,095,108 | 6/1978 | Inbar et al. .............. 250/369 |

OTHER PUBLICATIONS

Soussaline, et al., "Double and Triple Isotope Gamma Camera Studies with Energy Selection After Data Collection," presented at *Recent Advances in Nuclear Medicine*, Procedings of the First World Congress of Nuclear Medicine, Sep. 30–Oct. 5, 1974, Tokyo and Kyoto, Japan.

J. Svedberg, "Image Quality of a Gamma Camera System", *Phys. Med. Biol.*, 1968, vol. 13, No. 4, pp. 597–610.

J. Svedberg, "On the Intrinsic Resolution of a Gamma Camera System", *Phys. Med. Biol.*, 1972, vol. 17, No. 4, pp. 514–524.

J. Svedberg, "Computed Intrinsic Efficiencies and Modulation Transfer Functions for Gamma Cameras", *Phys. Med. Biol.*, 1973, vol. 18, No. 5, pp. 658–664.

J. Svedberg, "Computer Simulation of the Anger Gamma Camera", *Computer Programs in Biomedicine 4*, 1975, pp. 189–201.

J. Svedberg, "Improved Pulse Arithmetics for a Gamma Camera System", *Medical Radioisotope Scintigraphy*, proceedings of a Symposium on Medical Radioisotope Scintigraphy held by the International Atomic Energy Agency in Salzburg, Vienna, 1969, vol. I, pp. 125–134.

J. Svedberg, "Physical Aspects on the Anger Camera for Medical Diagnosis", Doctoral Thesis at Uppsala University, 1974.

*Primary Examiner*—Constantine Hannaher

[57] ABSTRACT

Coordinates of a light event, computed by signal processing equipment from output signals developed by an array of photodetectors of radiation imaging apparatus in response to the interaction of a radiation stimulus with a scintillation crystal, are validated only if a representation of the total energy of the light event lies within an energy window functionally related to the coordinates of the light event. In this manner, only desirable radiation stimuli interacting with the crystal are detected, and undesirable, indirect or scattered radiation stimuli interacting with the crystal are discriminated against.

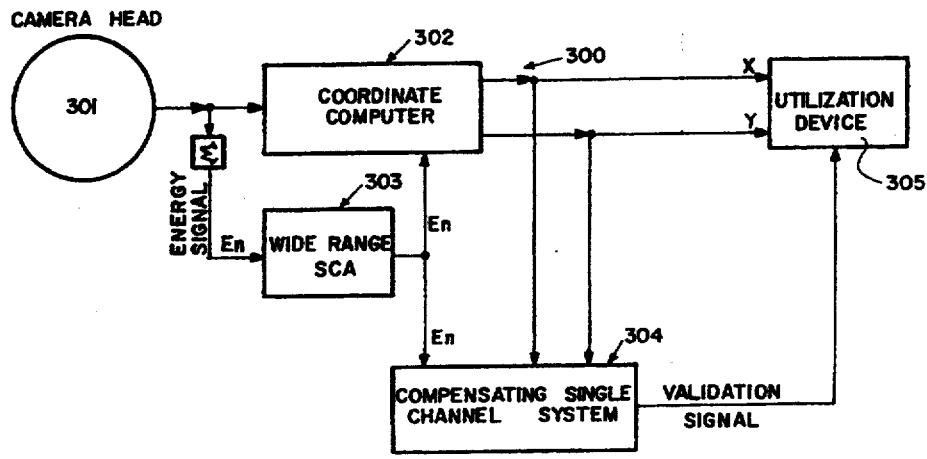

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-5 is confirmed.

* * * * *